United States Patent [19]

Samuels et al.

[11] 4,061,134
[45] Dec. 6, 1977

[54] ARTERIAL GRAFT DEVICE

[76] Inventors: Peter B. Samuels, 14708 Sutton St., Sherman Oaks, Calif. 91403; Ernest C. Wood, 2461 Ivanhoe Drive, Los Angeles, Calif. 9000

[21] Appl. No.: 626,070

[22] Filed: Oct. 28, 1975

[51] Int. Cl.² .......................... A61F 1/24; A61B 19/02
[52] U.S. Cl. ...................................... 128/1 R; 3/1.4; 206/438; 206/524.4
[58] Field of Search ............... 128/1 R, 334 R, 334 C, 128/335; 3/1, 1.4; 206/363, 438

[56] References Cited

U.S. PATENT DOCUMENTS

| 3,479,670 | 11/1969 | Medell | 128/334 R X |
| 3,514,791 | 6/1970 | Sparks | 128/334 R X |
| 3,562,820 | 2/1971 | Braun | 3/1.4 |
| 3,579,303 | 5/1971 | Pickering | 206/438 X |
| 3,648,295 | 3/1972 | Palma | 3/1 |
| 3,688,317 | 9/1972 | Kurtz | 3/1.4 |
| 3,862,886 | 1/1975 | Liner | 206/438 X |
| 3,911,918 | 10/1975 | Turner | 206/438 X |
| 3,918,099 | 11/1975 | Fuhr et al. | 3/1.4 X |
| 3,945,052 | 3/1976 | Liebig | 3/1 |

OTHER PUBLICATIONS

"The USCI Sauvage External Dacron Velour Prosthesis," Mar. 1973.

Primary Examiner—Edgar S. Burr
Assistant Examiner—Paul T. Sewell
Attorney, Agent, or Firm—McDougall, Hersh & Scott

[57] ABSTRACT

The preparation of an arterial graft from a device comprising a sealed chamber within an elongate housing formed of translucent impervious walls, an elongate tubular porous base member disposed within said sealed chamber formed of walls having axially spaced corrugations to enable the base member to be stretchable in the axial direction and bendable in all directions while preventing collapse to block the passage extending continuously therethrough, the means for introducing blood into the sealed chamber for clotting onto the walls of the base member to form the arterial graft.

22 Claims, 3 Drawing Figures

ARTERIAL GRAFT DEVICE

This invention relates to a new and improved arterial graft and particularly to grafts formed of cloth or plastic material and it relates to elements and to a method for the preparation of such arterial grafts.

Cloth and plastic grafts of the types described are permeable in their original construction so as to enable coating of the graft with blood obtained from the patient, as by coagulation of the blood to form a component lining the walls of the formed graft.

Coagulation to coat the graft with the patient's blood has been carried out by drawing blood from the patient into a bowl or receptacle to enable the blood to be mopped up by the graft and then worked to coagulate the blood on the otherwise porous surfaces of the graft.

This procedure is subject to a number of objections. It is an unsanitary, time consuming operation which requires an excessive amount of blood. The blood is exposed to bacteria and other microorganisms as well as to other contaminants in the atmosphere while the blood is being drawn into the bowl and while it is being mopped up by the graft.

The graft is exposed to the operating personnel, even though the nurses and physicians may be gowned and masked.

An excessive amount of blood is required to be drawn from the patient in order to have enough to be taken up by the graft and worked for clotting the blood sufficiently to coat the surfaces of the graft and considerable times is required for submersion of the graft in the pool of drawn blood and uniformly to distribute the blood and to clot the blood, uniformly to coat the surfaces of the graft.

It is an object of this invention to provide a device formed of cloth and/or plastic material in which the device can be rapidly wet out by the patient's blood without the need for handling the device; in which the amount of blood required for coagulation or clotting to coat the surfaces of the device is markedly reduced, and in which the operations to prepare the arterial graft from the device can be carried out under aseptic conditions by avoiding exposure to the environment until the prepared graft is removed immediately prior to use as an arterial graft.

These and other objects and advantages of this invention will hereinafter appear and, for purposes of illustration but not of limitation, embodiments of the invention are shown in the accompanying drawing in which —

Figure 1:
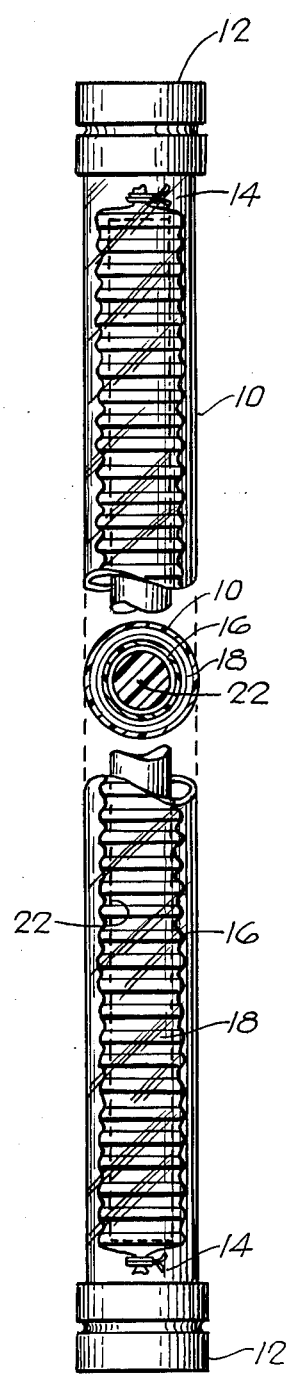
FIG. 1 is a plan view of a device adapted for use in the preparation of an arterial graft in accordance with the practice of this invention.

The invention will hereinafter be described with reference to the devices illustrated in the drawing. It will be understood that the concepts described will be capable of adaptation to other ramifications in devices and methods for preparation of the arterial graft.

Figure 2:
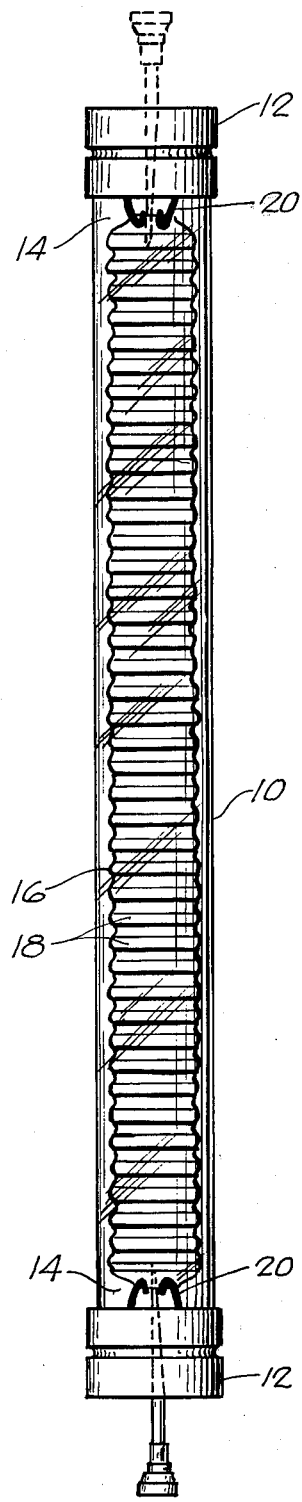
FIG. 2 is a plan view similar to that shown in FIG. 1 of a modification in the device for the preparation of an arterial graft in accordance with the practice of this invention.

With reference now to FIGS. 1 and 2 of the drawing, the device used in the preparation of the arterial graft, in accordance with the practice of this invention, comprises an elongate tubular member 10 sealed at each end, with at least one of the sealing members being in the form of a removable cap 12.

The tubular member 10 should be formed of a rigid, impermeable material, and preferably of a material which is either translucent or transparent so as to be able to observe the elements confined within the sealed chamber 14, but without introducing contamination into the chamber. For this purpose, the tubular member 10 may be formed by extrusion of such plastic materials as a polyacrylate or polyalkylacrylate, such as polymethylmethacrylate, polybutylmethacrylate and the like, polystyrene, polytetrafluoroethylene (Teflon), polyamide (Nylon), polyethylene, polypropylene or ethylene propylene copolymer, acrylic copolymers with styrene and/or butadiene, cellulose ethers or esters, such as cellulose acetate and the like, or of glass.

The end sealing members, such as the stoppers 12, should be formed of a plastic or elastomeric material which enables penetration of a needle for evacuation of the chamber 14 and/or for introduction of blood into the chamber and in which the chamber is resealed upon removal of the needle or other penetration means used to communicate the interior of the chamber with a vacuum source, or with a blood bottle or artery for transmission of the patient's blood into the chamber.

Suspended within the chamber 14 is an elongate pervious member 16 which forms the base of the arterial graft. The member 16 can be woven of a textile material, using natural or synthetic fibers such as nylon, dacron, rayon, and the like, or it can be fabricated of a plastic material, such as cellulose acetate, cellulose butyrate, and the like. The member 16 is in the form of an elongate tubular member dimensioned to have a length slightly less than the length of the enclosed chamber 14 and a diameter which is less than the internal diameter of the tubular housing 10 so as to provide for free annular space therebetween.

The tubular base member 16 is formed with corrugations 18 substantially throughout its length to provide stretchability in the axial direction and bendability in every direction, while preventing collapse which would result in closure of the passage which must extend continuously through the graft notwithstanding any configuration or shape acquired by the graft in use. The corrugations 18, which are preferably in the form of axially spaced circumferential ribs, formed in the walls of the tubular base member 16, enable the base member to be stretched thereby to open the interstices of the porous fabric for better penetration and more complete occlusion of the interstices during clotting of the blood.

The tubular base member 16 can be suspended within the chamber 14 in a stretched condition by the use of stainless steel wire hooks 20 which interconnect the ends of the porous base member with the adjacent stoppers 12, or other sealing member, as shown in FIG. 2. Instead, the tubular base member 16 can be maintained within the chamber, in a stretched condition, by means of a rigid rod 22 formed of glass or plastic material dimensioned to have a length greater than the length of the relaxed base member 16 for less than the length of the chamber 14, and an external diameter less than the internal diameter of the corrugated base member to enable the rod 22 to extend through the interior of the base member with the ends of the base member tied over or otherwise secured to the ends of the rod, as illustrated in FIG. 1.

The modification in which use is made of the base member 16 stretched about the rod 22 has the advantage of reduced free volume within the chamber with corresponding reduction in the amount of blood used to fill the chamber in the preparation of an artificial graft.

When the chamber is pre-evacuated, it is only necessary to insert a hollow needle through the stopper 12 at one end while the other end of the needle is connected either to a blood bottle containing the patient's blood or to an artery of the patient, whereby the patient's blood is drawn into the chamber.

Instead, the patient's blood can be forceably introduced into the chamber by injection through one of the rubber stoppers 12.

By way of a preferred modification, the chamber may be operated as a syringe in which a hollow needle extending through the stopper at one end is connected to a vacuum source while a hollow needle extending through the sealing member at the other end is connected to a blood bottle containing the patient's blood or directly to an artery of the patient. Instead of making use of a vacuum source, one needle can be inserted into a vein operating at low pressure while the other needle is inserted into an artery operating at high pressure so that the patient's blood will flow naturally from the high pressure arterial system toward the low pressure venous system and into the chamber.

When the necessary amount of patient's blood, or other blood, has been received within the chamber 14, the hollow needles are removed to re-seal the chamber and the tubular member rocked or otherwise agitated to cause distribution of the blood for complete and uniform permeation of the base member and clotting to form a lining in the form of a coating which permeates the interstices of the base member.

When completely permeated, the formed graft, still sealed within the chamber, can be set aside until use is to be made of the prepared graft. At that time, the sealing members can be removed to make the prepared graft available for use as an arterial graft or the like.

It will be apparent from the description that preparation of the graft is achieved under aseptic conditions in that neither the blood nor the elements making up the graft are exposed to atmospheric conditions and neither is touched by any personnel during preparation of the graft.

By way of modification to enhance the characteristics of the graft and its preparation, the base member 16 can be coated with a non-wettable substance, such as a liquid silicone or wax.

The base member can be treated to coat the surfaces with an antibiotic to minimize undersirable enzymatic reactions and to destroy undesirable microorganisms which might be present in the blood clotted on the base member in forming the graft.

The base member can be pre-treated with anticoagulant to prevent undesirable coagulation of the blood before complete coating of the base member and occlusion of the interstices has been achieved.

Figure 3:
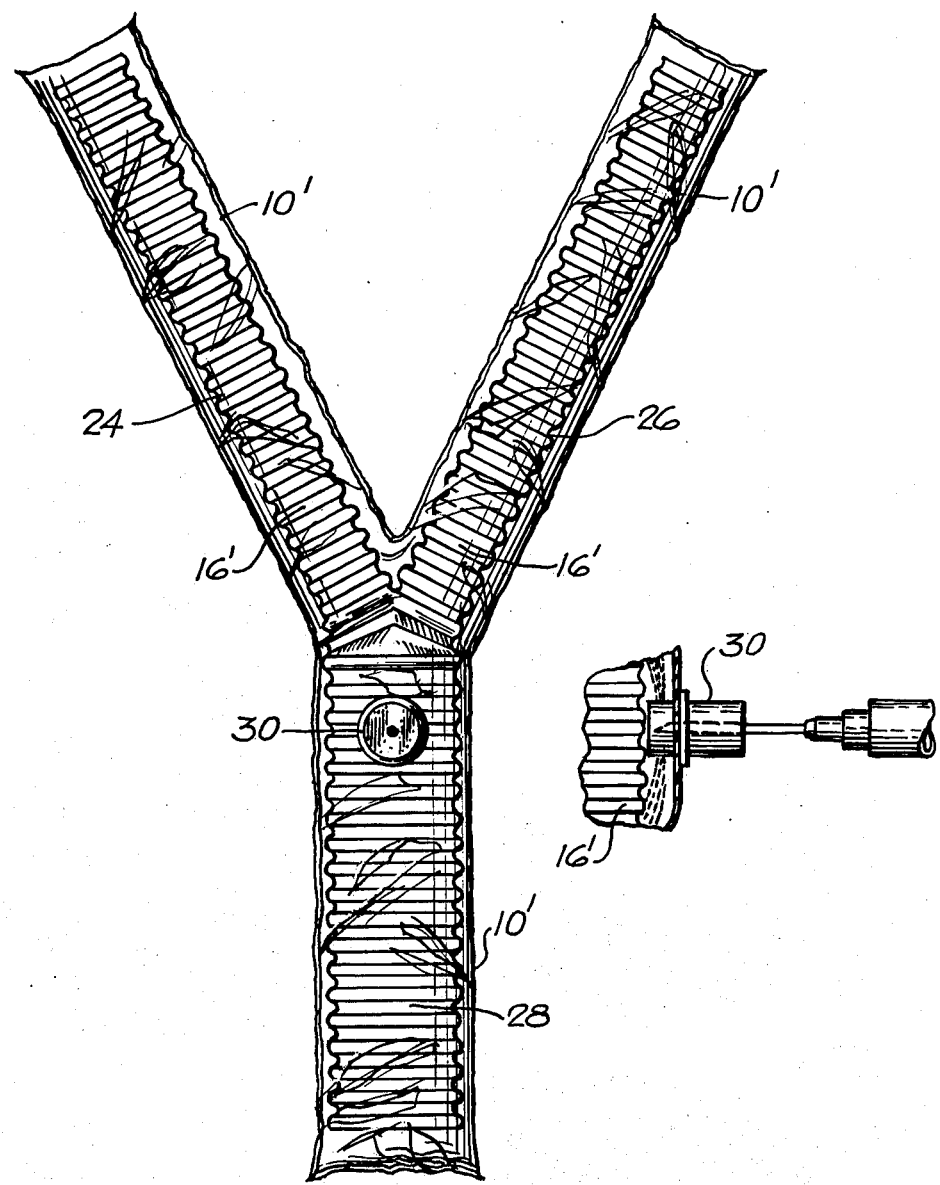
FIG. 3 is a plan view of a further modification of the device of this invention.

In the modification shown in FIG. 3, the porous base member 16' is housed within a chamber 10' formed of a flexible, impervious plastic material which enables the elements to be worked with the blood introduced into the chamber for lining the walls of the base member to form the graft. In the illustrated modification, the base member 16' is in the form of a forked member in which two separate legs 24 and 26 extend from a single section 28 to provide a branched arterial graft in which the passages through the forked members communicate directly with the passage through the single section. Both sections are corrugated substantially throughout their length and are formed of a flexible porous material such as of cloth or plastic of the types previously described.

The confining chamber 10', in the form of a sack, is fabricated of a transparent, impervious plastic material which is highly flexible to enable the assembly to be worked. For this purpose, the sack can be formed by heat sealing the edges of a thin strip of plastic material such as cellulose acetate, cellulose butyrate, polyethylene, polypropylene, ethylene propylene copolymer and the like.

Access to the interior of the sack is provided by means of a valve member 30 which can be penetrated by a hollow needle or through which the patient's blood can be otherwise introduced into the interior of the sack.

In this modification, after the patient's blood has been introduced, the sack is worked uniformly to distribute the blood for coating the walls of the base member. Thereafter the unit can be set aside until it is desired to make use of the prepared graft.

It will be understood that changes may be made in the details of construction, arrangement and operation without departing from the spirit of the invention, especially as defined in the following claims.

We claim:

1. A device for use in the preparation of a graft for blood vessels comprising a sealed chamber within an elongate housing formed of impervious walls, an elongate tubular porous base member disposed within said sealed chamber the walls of which are formed with axially spaced corrugations to enable the base member to be stretchable in the axial direction and bendable in all directions while militating against collapse to block the passage extending continuously through the base member, means for introducing blood into the sealed chamber for clotting onto the walls of the base member while confined within the sealed chamber, and means for gaining access to the interior of the chamber for removal of the base member after the blood has been clotted onto the walls thereof.

2. A device as claimed in claim 1 in which the housing is in the form of an elongate, rigid tubular member open at both ends and which includes closure means for sealing the open ends of the tubular member.

3. A device as claimed in claim 2 in which the closure means comprises sealing plugs which fit into the open ends of the tubular member.

4. A device as claimed in claim 1 in which the housing is in the form of a flexible sack of thin translucent impervious material.

5. A device as claimed in claim 1 which includes means for suspending the tubular base member within the sealed chamber.

6. A device as claimed in claim 5 in which the means for suspending the tubular member within the sealed chamber comprises clip members interconnecting the ends of the tubular base member with the means sealing the ends of the tubular housing.

7. A device as claimed in claim 1 which includes means for maintaining the tubular base member in an axially stretched state within the sealed chamber.

8. A device as claimed in claim 7 in which the means for maintaining the tubular base member in a stretched state comprises clip means connecting the ends of the tubular base member to the respective ends of the tubular housing.

9. A device as claimed in claim 7 in which the means for maintaining the tubular base member in the stretched state comprises an elongate rigid rod-like member extending through the passage of the tubular base member and dimensioned to have a length greater than the normal length of the tubular base member and means securing the ends of the tubular base member about the ends of said rod.

10. A device as claimed in claim 1 in which the housing is formed of a translucent plastic.

11. A device as claimed in claim 1 in which the tubular base member is formed of a textile material.

12. A device as claimed in claim 1 in which the tubular base member is formed of a plastic material having porous walls.

13. A device as claimed in claim 1 in which a vacuum exist within the sealed chamber.

14. A device as claimed in claim 1 which includes a rod-like member within the base member to reduce the free volume within the chamber.

15. A device as claimed in claim 1 which includes means for drawing a vacuum.

16. A device as claimed in claim 1 which includes means communicating the chamber with a source of patient's blood.

17. A device as claimed in claim 1 which includes a coating of a non-wettable material on the base member.

18. A device as claimed in claim 17 in which the non-wettable material is a liquid silicone.

19. A device as claimed in claim 17 in which the non-wettable material is a wax.

20. A device as claimed in claim 1 which includes an antibiotic on the surfaces of the base member.

21. A device as claimed in claim 1 which includes an anticoagulant as a coating on the base member.

22. A device as claimed in claim 1 in which the base member comprises a unitary member in the form of an elongate section from which separate leg sections extend with the interior of the leg sections communicating directly with the interior of the elongate section.

* * * * *